(12) United States Patent
Kober et al.

(10) Patent No.: US 6,451,739 B1
(45) Date of Patent: Sep. 17, 2002

(54) AQUEOUS GROWTH-REGULATING COMPOSITIONS

(75) Inventors: Reiner Kober, Fussgönheim; Wilhelm Rademacher, Limburgerhof; Peter Höppner, Neustadt; Ulrich Kiessling, Neuhofen; Jürgen Scholz, Mannheim; Rainer Berghaus; Oliver Borzyk, both of Speyer; Günter Oetter, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/744,719

(22) PCT Filed: Jul. 12, 1999

(86) PCT No.: PCT/EP99/04871

§ 371 (c)(1),
(2), (4) Date: Jan. 30, 2001

(87) PCT Pub. No.: WO00/07445

PCT Pub. Date: Feb. 17, 2000

(30) Foreign Application Priority Data

Jul. 31, 1998 (DE) .......... 198 34 543

(51) Int. Cl.$^7$ .......... A01N 25/30; A01N 33/12; A01N 43/40; A01N 43/58; A01N 43/84

(52) U.S. Cl. .......... 504/224; 504/236; 504/248; 504/345; 504/358

(58) Field of Search .......... 504/224, 236, 504/248, 345, 358

(56) References Cited

U.S. PATENT DOCUMENTS

| | | | |
|---|---|---|---|
| 4,525,200 A | 6/1985 | Kimpara et al. | 71/76 |
| H224 H | 3/1987 | Malik et al. | 71/92 |
| 5,681,949 A | 10/1997 | Johansson et al. | 536/123 |
| 5,705,648 A | 1/1998 | Clark et al. | 546/349 |
| 5,750,513 A | 5/1998 | Hoorne et al. | 514/54 |
| 5,958,104 A * | 9/1999 | Nonomura et al. | 71/11 |
| 6,255,250 B1 * | 7/2001 | Finch et al. | 504/138 |

FOREIGN PATENT DOCUMENTS

| | | |
|---|---|---|
| CA | 2300858 | 2/1999 |
| CA | 2248979 | 4/1999 |
| DE | 26 09 105 | 9/1977 |
| DE | 197 35 790 | 2/1999 |
| EP | 573 177 | 12/1993 |
| GB | 1 573 215 | 8/1980 |
| WO | WO 94/12259 | 6/1994 |
| WO | WO 94/21655 | 9/1994 |
| WO | WO 99/09832 | 3/1999 |
| WO | WO 99/20106 | 4/1999 |

* cited by examiner

*Primary Examiner*—S. Mark Clardy
(74) *Attorney, Agent, or Firm*—Keil & Weinkauf

(57) ABSTRACT

The present invention relates to aqueous homogeneous compositions in the form of active quaternary ammonium compound concentrates such as mepiquat or chlormequat, for regulating plant growth, and to the use of these active compound concentrates for preparing aqueous spray solutions having increased activity.

18 Claims, No Drawings

AQUEOUS GROWTH-REGULATING COMPOSITIONS

The present invention relates to aqueous homogeneous compositions in the form of active compound concentrates for regulating plant growth having an active compound concentration of at least 20%, and to the use of these active compound concentrates for preparing aqueous spray solutions having increased activity.

Active compounds which regulate plant growth can have various effects on virtually all development stages of a plant, and they are therefore used as growth regulators. Such active compounds have a number of different application possibilities, for example in plant cultivation, in agriculture and in horticulture. With their aid, it is possible to strongly inhibit the vegetative growth of the plants, which is manifested in particular in a reduction in the longitudinal growth. The treated plants therefore have a stocky growth; additionally, a darker leaf coloration is observed. Advantageous for practice is a reduced intensity of the growth of grasses on roadsides, hedges, canal embankments and on greens such as parks, playing fields, fruit plantings, ornamental lawns and airfields, so that it is possible to reduce the labor- and cost-intensive grass cutting.

It is also of economic interest to increase the resistance to lodging of crops which are prone to lodging, such as cereals, maize and sunflowers. The culm shortening and culm strengthening caused in this case reduce or eliminate the risk of lodging (of falling over) of plants under unfavorable weather conditions before harvesting. The application of growth regulators for inhibiting the longitudinal growth and for temporally altering the course of ripening in cotton is also important. Completely mechanized harvesting of this important crop plant is thus made possible. In the case of fruit and other trees, pruning costs can be reduced using the growth regulators. In addition, the alternation of fruit trees can be broken by means of growth regulators. Using growth regulators, it is also possible to increase or inhibit the lateral branching of the plants. This is of interest where, for example in the case of tobacco plants, the formation of side shoots (suckers) is to be inhibited in favor of leaf growth.

In the case of winter rape, for example, it is also possible to considerably increase the frost resistance by using growth regulators. In this case, on the one hand, the longitudinal growth and the development of an excessively luxuriant (and thereby particularly frost-susceptible) foliage or biomass are inhibited. On the other hand, after sowing and before the winter frosts set in, the young rape plants are held back in their vegetative development in spite of favorable growth conditions. As a result, the frost-susceptibility of plants which are prone to premature degeneration of the inhibition of flowering and to transition into the generative phase is also eliminated. In other crops as well, for example in winter grain, it is advantageous if the populations are well tillered by treatment with the growth regulators in the fall, but are not too luxuriant when going into the winter. It is thus possible to prevent increased frost sensitivity and, because of the relatively low foliage or biomass, attack by various diseases (for example fungal diseases). Moreover, in the case of many crop plants, it is possible to plant the soil more densely by inhibiting vegetative growth, so that higher yields per area can be achieved.

With the aid of growth regulators, it is possible to obtain higher yields both of parts of plants and of plant constituents. Thus, it is also possible, for example, to induce the growth of greater amounts of buds, flowers, leaves, fruits, seeds, roots and tubers, to increase the sugar content in sugarbeet, sugarcane and citrus fruits, to increase the protein content in grain or soybeans or to stimulate rubber trees to an increased flow of latex. In this case, the active compounds can cause increases in yield by intervention in the plant metabolism or by promoting or inhibiting vegetative and/or generative growth. Finally, both shortening or prolongation of the development stages and acceleration or retardation of the ripening of the harvested parts of plants before or after harvesting can be achieved using plant growth regulators.

Of economic interest is, for example, the facilitation of harvesting, which is made possible by the temporally concentrated fall or decrease in the adhesiveness to the tree in the case of citrus fruits, olives or in the case of other species and varieties of pomes, drupes and indehiscent fruit. The same mechanism, i.e. the promotion of the formation of abscission tissue between the fruit or leaf and shoot part of the plant is also essential for a well-controlled defoliation of useful plants, such as, for example, cotton.

The water consumption of plants can furthermore be reduced using growth regulators. This is particularly important for areas under agricultural cultivation which have to be irrigated artificially at high cost, for example in arid or semiarid regions. By using growth regulators, the intensity of irrigation can be reduced, and a more cost-effective management procedure can be carried out. Under the influence of growth regulators, the water that is available is utilized more effectively since, inter alia, the opening width of the stomata is reduced, a thicker epidermis and cuticle are formed, the root penetration of the soil is improved, the transpiring leaf surface is reduced, or the microclimate in the crop plant population is favorably effected by a more compact growth.

Growth-regulating active compounds which are used in the sector of agriculture are, inter alia, N,N,N-trimethyl-N-β-chloroethylammonium chloride (CCC, chlorocholine chloride, chlormequat, DE 12 94 734), N,N-dimethylmorpholinium chloride (DMC, DE 16 42 215) and N,N-dimethylpiperidinium chloride (DPC, MQC, mepiquat chloride, DE 22 07 575). These active compounds, in particular chlormequat chloride and mequat chloride, are typically employed in the cultivation of cereals, at relatively high application concentrations. The application rate of these active compounds per application is generally 0.3–1.5 kg/ha. The products are commercially available as aqueous active compound concentrates, tablets or granules (for example PIX®, PIX® DF, BASF Corporation).

With a view to the fact that the active compounds are employed at relatively high application rates, there is a demand for highly concentrated active compound formulations which are diluted with the required amount of water immediately prior to use. However, highly concentrated active compound solutions are problematic, since it is generally necessary to add various additives to the formulations for stabilization and/or for enhancing the activity. As a result, there are frequent incompatibilities of the individual additives and/or active compounds with one another, so that unstable formulations are obtained which are characterized by the occurrence of turbidity, precipitation of the additives or active compounds or by poor storage stability. If the total concentration of additives and active compounds exceeds a certain maximum value, there are often further disadvantageous effects, such as, for example, phase separation, sedimentation or even more pronounced turbidity. These mixing incompatibilities are either noticeable directly, by the occurrence of a two-phase system, or they result, in the longer term, in a reduced storage stability of the solutions. Under these circumstances, it is often no longer possible to add the desired or required additives in total to the ready-made-up formulation, so that the additives have to be supplied to the user in separate containers. The user mixes the concentrates with the other additives, dilutes them with water and adds them to the tank or spray container immediately prior to use. In principle, this constitutes a disadvantage in the handling of such formulations, since an additional operation is required. Additionally, in the case of improper and negligently erroneous use (for example, mixing errors, dilution errors etc.), a safer and more optimum application of the crop protection agent is not ensured.

An alternative possibility for preparing highly concentrated solutions is the use of organic solvents instead of water for preparing highly concentrated solutions of the active compounds mentioned at the outset. However, this is undesirable for ecological reasons. WO 96/22020 and DE 44 45 546, for example, disclose activity-enhancing non-water-soluble oils and esters, such as, for example, esters of adipic acid, oleic acid or stearic acid, which can be used as tank mix additives for preparing formulations of the O/W-type (oil-in-water). However, in the case of the active compounds mentioned at the outset, these formulations have the disadvantage that it is only possible with great difficulty to stabilize the oil phase with respect to a separation of the oil/water phase, since suitable thickeners, for example from the xanthane series, are generally not sufficiently effective if high proportions of electrolyte are present.

Likewise, it is not possible to prepare cost-effective and simple solids formulations readily, since the active compounds are very hygroscopic and therefore require a high proportion of additives for stabilization or for activity enhancement. Owing to the resulting high amounts of crop protection agents, such solids formulations are disadvantageous.

It is an object of the present invention to provide stable homogeneous active compound concentrates on an aqueous base which have a very high proportion of active compound and which furthermore contain an activity-enhancing proportion of additives. The active compound concentrates should enable the end user to apply them in a simple, safe and efficient manner.

We have found that this object is achieved by providing aqueous, active-compound-containing compositions in the form of active compound concentrates having an active compound concentration of at least 20%, which comprise a) at least one active compound of the formula I

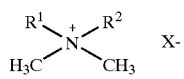

(I)

and b) at least one auxiliary selected from the group consisting of
b1) alkylglucosides,
b2) alkylsulfonates or alkylarylsulfonates of the formula II

where $R^3$ is an aliphatic group having 6–24 carbon atoms, $C_6$–$C_{16}$-alkylphenoxypolyethoxy, $C_1$–$C_{16}$-alkylphenyl, $C_1$–$C_{16}$-alkylnaphthyl and M is a mono- or divalent cationic group; or b3) quaternary ammonium salts of the formula III

$R^4$ is $C_6$–$C_{24}$-alkyl;
$R^5$ is hydrogen, $C_1$–$C_{24}$-alkyl, benzyl, $C_1$–$C_{12}$-alkylbenzyl or hydroxypolyethoxyethyl,
$R^6$ has the same meaning as $R^5$, $R^5$ and $R^6$ being identical or different,
A is $C_1$–$C_6$-alkylene or $C_1$–$C_6$-alkyleneaminocarbonyl,
X is an anionic group.

Surprisingly, it has been found that, by adding an auxiliary from the group of the auxiliaries mentioned under point b1), b2) or b3), monophasic aqueous homogeneous active compound formulations are obtained. The concentration of the active compounds in the solution is up to 70%, preferably up to 60% or 50% (hereinbelow, the percentages are in each case based on percentages by weight, unless indicated otherwise). The solutions are provided in particular as concentrates having an active compound concentration of at least 20%, preferably at least 30% or 40%. Hitherto, it has not been possible to prepare such concentrated monophasic active compound solutions since the addition of customary additives resulted in biphasic systems (phase separation). In contrast, the formulations according to the invention have a very good mixing compatibility between the individual additives and the active compounds of the formula I. The resulting compositions are stable, homogeneous and monophasic.

Furthermore, it has surprisingly been found that the additives selected according to the invention (cf. the groups defined at the beginning under b1), b2) or b3)) increase the biological activity of the compounds of the formula I. Moreover, they serve as solubilizers for surface-active substances, in particular for nonionic surfactants. Owing to this, it is possible to add more of these additives to the liquid formulations. An increased addition is an advantage, since this achieves a further activity enhancement of the compounds of the formula I compared to formulations not having these additives. The required application rate of the active compounds of the formula I in agriculture can thereby be reduced considerably. For example, a reduction of the amount of active compound by at least 10%, in some cases even by at least up to 30% or at least up to 50% could be achieved, with comparable biological activity. In exceptional cases even a reduction by up to 80% of the application rate is possible. In cereals, for example, the active compound application rate can thus be reduced to a value of 0.1–1.5 kg/ha. Thus, in the case of summer wheat, for example, a comparable biological effect (reduction of longitudinal growth) could be achieved using an application rate of 0.5 kg of active compound/ha, whereas without addition of the additives according to the invention an application rate of 2 kg/ha was required to obtain a comparable effect. This corresponds to a reduction in the application rate by 75%. The corresponding application rate for cotton, for example, is 0.001–0.1 kg/ha. In principle, the application rate varies for different plants and is adapted to the particular requirements and climatic conditions. However, with the aid of the compositions according to the invention, an appropriate reduction in comparison to the otherwise customary application rate is achieved in all cases. A further advantage of the formulations according to the invention consists in the fact that the proportion of other additives can be reduced, or is no longer required. The concentrates according to the invention preferably essentially consist of an active compound of the formula I, one of the abovementioned auxiliaries b1)–b3) or mixtures of these auxiliaries, and water, in the absence of other additives.

Using the additives selected according to the invention, it is possible to prepare finished formulations of the active compounds of the formula I which also comprise in particular nonionic surfactants, such as, for example, ethylene oxide/propylene oxide block copolymers. The preparation of finished formulations comprising nonionic surfactants has hitherto been possible only with difficulty. Surprisingly, the additives according to the invention act as excellent solubilizers for these nonionic surfactants. Thus, for example, by using a 10–30% proportion of the additives according to the invention it is possible for 10–30% of other activity-enhancing additives to be present in these finished formulations. The further addition of such additives as wetters, spreading agents, wetting agents or other auxiliaries accelerates the uptake of active compounds in the leaves of the plants, and therefore makes it possible to use less of the crop protection agents.

The formulations according to the invention are furthermore advantageous from an ecological point of view, since the alkylglucosides are additives which are prepared from renewable raw materials (sugars). Alkylglucosides comprise a high proportion of hexoses which are rapidly degraded in nature and are therefore particularly advantageous with regard to environmental compatibility when used in agriculture. In this manner, the application of purely synthetic additives on the outdoor areas can be reduced.

Owing to the fact that the formulations according to the invention comprise high concentrations of the active compounds, it is finally also possible to save packaging costs, transport costs or storage costs in comparison to the crop protection agents which usually have to be employed in larger amounts.

In the context of the present invention, the active compounds used are compounds of the formula I

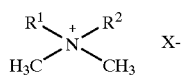

(I)

where $R^1$, $R^2$ and X are as defined below:

$R^1$ is $C_1$–$C_4$-alkyl;

$R^2$ is $C_1$–$C_4$-alkyl, cyclopentenyl, halo-$C_1$–$C_6$-alkyl;

or $R^1$ and $R^2$ together are a radical —(CH$_2$)$_5$—, —(CH$_2$)$_2$—O—(CH$_2$)$_2$— or —(CH$_2$)—CH=CH—(CH$_2$)—NH—;

X is an anionic group.

Suitable $C_1$–$C_4$-alkyl groups are, for example, methyl, ethyl, isopropyl. The preferred halo-$C_1$–$C_6$-alkyl group is the 2-chloroethyl group. $R^1$ and $R^2$ together with the nitrogen atom to which they are attached preferably form a morpholino or piperidino group. X is, for example, a halide, such as chloride, bromide; sulfate; $C_1$–$C_4$-alkyl sulfate, such as methyl sulfate; $C_1$–$C_4$-alkylsulfonate, such as methylsulfonate; or another anionic group which is agriculturally utilizable. In principle, bivalent anionic groups, which are employed in the appropriate stoichiometric amounts to the ammonium cation, are also suitable. Preferred active compounds of the formula I are N,N,N-trimethyl-N-β-chloroethylammonium chloride (CCC, chlorocholine chloride, chlormequat), N,N-dimethylmorpholinium chloride (DMC) and N,N-dimethylpiperidinium chloride (DPC, MQC, mepiquat chloride).

The additives selected according to the invention are water-soluble additives which have a stabilizing and/or activity-enhancing effect on the active compounds of the formula I. In the context of the present invention, alkylglucosides (cf. the group defined at the beginning under point b1)), alkylsulfonates or alkylarylsulfonates (cf. the group defined at the beginning under b2)), and/or selected quaternary ammonium salts (cf. the group defined at the beginning under point b3)) are suitable for this purpose.

Alkylglucosides (frequently also referred to as alkylpolyglucosides in the literature) is a collective term for the complex reaction products obtainable by an acid-catalyzed reaction of glucose or starch and alcohol (Fischer reaction), and their composition is determined mainly by the reaction ratio of glucose to alcohol. A main component of the alkylglucosides is the alkylmonoglucoside, a mixture of alkyl-α-D- and alkyl-β-D-glucopyranoside and small amounts of the corresponding glucofuranoside. The corresponding alkyldiglucosides (isomaltosides, maltosides, etc.), alkyloligoglucosides (maltotriosides, maltotetraosides, etc.), and oligomeric or polymeric glucose are also present, in varying amounts. The alkylglucosides may be monoglucosides or polyglucosides or mixtures thereof. Here, the alkylglucoside unit can be characterized by the formula R—O—S, where S is a saccharide group, and R is a saturated or mono- or polyunsaturated branched or linear alkyl group having 4- 24 carbon atoms. In the literature, the long-chain alkylglucosides are also referred to as fatty alkylglucosides (derived from the corresponding fatty alcohols). The saccharide units are derived from the following sugar units: fructose, glucose, mannose, galactose, telose, gulose, allose, altrose, idose, arabinose, xylose, lyxose and/or ribose, and mixtures thereof. The group S is usually derived from glucose units, so that the products are consequently referred to as glucosides. The degree of polymerization of the alkylglucosides is generally 1.1–8, preferably 1.3–2. In industrial production, the alkylglucosides are generally obtained as approximately 50–70% strength aqueous concentrates. Depending on the preparation process, they contain small amounts of butylglucoside, unreacted alcohols or fatty alcohols, carbohydrates or oligocarbohydrates. A number of alkylglucosides is commercially available (for example under the tradenames APG 225, APG 300, Triton® BG, Lutensol® GD 70 (N-decyl-α-D-glucopyranoside, BASF AG), AG 6202(a 2-ethylhexylglucoside, Akzo). Other alkylglucosides are classified, for example, under CAS Reg. Nos. 29781-81-5; 29781-80-4; 59947-99-8; 54549-23-4. Processes for preparing alkylglucosides are disclosed in WO 94/21665; EP 0 635 022 and EP 0 616 611.

Preferred auxiliaries from the group of the alkylglucosides (group b1)) for the purpose of the present invention are, for example, the following: AG 6202 (2-ethylhexylglucoside); Lutensol®, in particular Lutensol® GD 65 or Lutensol® GD 70 (a fatty alcohol glucoside); Simusol®, in particular Simusol® SL 8 (an alkylglucoside, CAS No. 68515-73-1) or Simusol® SL 62 (an alkylglucoside).

In the context of the present invention, alkylsulfonates and alkylarylsulfonates are compounds of the formula II

(II), where $R^3$ is an aliphatic group having 6–24 carbon atoms which may be straight-chain or branched and saturated or mono- or polyunsaturated, or is a $C_6$–$C_{16}$- alkylphenoxypolyethoxy group having up to 50 oligo- or polyethoxy units. In the context of the present invention, compounds of the formula II are, for example, alkylsulfonates, fatty alkylsulfonates, alkylarylsulfonates, fatty alkylarylsulfonates or alkylphenol polyoxyether sulfates. Particularly suitable are selected aliphatic sulfonates, alkylarylsulfonates or alkylphenoxy ether sulfates. M is a mono- or divalent cationic group, for example ammonium, sodium, potassium, magnesium or calcium. Preferred auxiliaries from the group of the alkylsulfonates and alkylarylsulfonates (group b2)) for the purpose of the present invention are, for example, the following: Rewoquat®,in particular Rewoquat® CPEM (cocospentaethoxymethylammonium methosulfate) or Rewoquat® RTM 50 (ricinoleic acid propylamidotrimethylammonium methosulfate); Protecol®, in particular Protecol® KLC 50 (dimethyl-n-alkyl-benzylammonium chloride).

In the context of the present invention, quaternary ammonium salts are compounds of the formula III

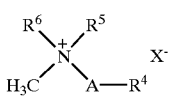

(III)

where:
- $R^4$ is $C_6$–$C_{24}$-alkyl;
- $R^5$ is hydrogen, $C_1$–$C_{24}$-alkyl, benzyl, $C_1$–$C_{12}$-alkylbenzyl, or hydroxypolyethoxyethyl,
- $R^6$ has the same meaning as $R^5$, $R^5$ and $R^6$ being identical or different,
- A is $C_1$–$C_6$-alkylene or $C_1$–$C_6$-alkyleneaminocarbonyl,
- X is an anionic group, for example chloride, sulfate, methosulfate, $C_2$–$Cl_6$-alkylsulfonate, $C_2$–$Cl_6$-alkyl sulfate, phenylsulfonate, naphthylsulfonate, $C_1$–$C_{24}$-alkylphenyl-sulfonate, $C_1$–$C_{24}$-alkylnaphthylsulfonate.

The abovementioned long-chain alkyl groups having 8 or more carbon atoms are also referred to as fatty alkyl groups in the literature. In the definition of $R^5$ and $R^6$, hydroxypolyethoxyethyl groups are preferably those groups which have a chain length of 0–10 units. In the definition of A, an alkylene group is preferably a methylene, ethylene or propylene group.

Preferred auxiliaries from the group of the quaternary ammonium salts (group b3)) for the purpose of the present invention are, for example, the following: Wettol®, in particular Wettol® EM 1 (dodecylbenzenesulfonic acid, Ca salt) or Wettol® EM 11 (Ca alkylarylsulfonate); Emulphor®, in particular Emulphor® OPS 25 (octylphenol-(EO)$_{25}$-sulfate, Na salt); Lutensit® in particular Lutensit® A-E S (isononylphenol tetraethoxysulfate, Na salt) or Lutensit® A- PS (alkylsulfonate, Na saslt); ALBN 50 (dodecylbenzenesulfonate, Na salt).

The compositions according to the invention may furthermore also contain one or more of the following additives a)–d):

a) up to 30%, in particular up to 25%, of anionic, cationic or nonionic surfactants.

b) up to 35%, in particular up to 20%, of inorganic ammonium salts, such as ammonium sulfate, ammonium nitrate, ammonium chloride, ammonium phosphate or other minerals or trace elements which can be utilized by plants.

c) up to 30%, in particular up to 20%, of straight-chain or branched $C_3$–$C_{12}$-alkylcarboxylic acids, $C_3$–$C_{12}$-di- or tricarboxylic acids, such as, for example, propionic acid, pelargonic acid or 2-ethylhexanoic acid, and their agriculturally useful alkali metal or alkaline earth metal or ammonium salts, such as, for example, potassium salts or calcium salts.

d) up to 40%, in particular up to 25%, of other active compounds from the field of crop protection, such as, for example, other growth-regulating active compounds, in particular ethephon.

The compositions according to the invention contain a maximum of up to 70% of water, preferably up to 50% or up to 30% of water, based on the total weight of the liquid formulation. The proportion of water in percent is preferably 20–40%, based on the total weight of the formulation.

Suitable surfactants in the context of the additives mentioned above under point a) are customary surface-active substances which can be used in agriculture. Examples which may be mentioned are the following: alkali metal, alkaline earth metal and ammonium salts of aromatic sulfonic acids, for example lignin-, phenol-, naphthalene- and dibutylnaphthalenesulfonic acid, and also of fatty acids, alkyl- and alkylarylsulfonates, alkyl, lauryl ether and fatty alcohol sulfates, and salts of sulfated hexa-, hepta- and octadecanols, and of fatty alcohol glycol ethers, condensation products of sulfonated naphthalene and its derivatives with formaldehyde, condensation products of naphthalene or of naphthalenesulfonic acid with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

The finished formulations according to the invention are obtained by mixing the solid active compounds or their aqueous highly concentrated solutions with the auxiliaries. Preferably, for example, aqueous solutions of active compound in a concentration of 50–80% are initially charged, and the auxiliaries are incorporated with stirring. The concentration of the active compounds in the highly concentrated solutions is approximately at least 100 g/l, preferably at least 200 g/l, up to a maximum of approximately 700 g/l, preferably in the range between 200–600 g/l.

Active compound concentrates in the context of the present invention are aqueous solutions of active compounds and the additives according to the invention, the total concentration of active compounds being at least 20% (percent by weight per unit of volume, for example 200 g/l), in particular at least 30% (300 g/l). The total concentration of active compounds is at most up to 70% (700 g/l), preferably up to 60% (600 g/l). The concentrates contain at least one active compound of the formula I. In addition to the active compounds of the formula I, the solution of active compounds may also comprise other active compounds for treating plants, such as, for example, growth-regulating active compounds, fertilizers, herbicides or fungicides. The content of compounds of the formula I in mixtures is at least 5%, preferably at least 10% or 20%. Other active compounds which can be employed are, for example, other active compounds, such as, for example, herbicides, fungicides or growth-regulating active compounds. A preferred further active compound is ethephon [sic] (2-chloroethylphosphonic acid). The concentration of this active compound is, for example, 50–400 g/l (5–40%) in the finished formulation, i.e. in the aqueous concentrate.

Preferred active compounds of the formula I are N,N,N-trimethyl-N-β-chloroethylammonium chloride (CCC) or N,N-dimethylpiperidinium chloride. CCC is employed for preparing the compositions according to the invention in the form of a highly concentrated solution of 750 g/l, for example. Starting from this highly concentrated solution, the active compound concentrates according to the invention are prepared with the aqueous solutions of the additives from the group b1), b2) or b3) by dilution [sic]. In the case of CCC, for example, 8 parts by volume of the highly concentrated concentrate (750 g/l) are mixed with 2 parts by volume of the aqueous solution of the selected additive, resulting in an active compound concentration of CCC in the active compound concentrate according to the invention of 600 g/l (60%). The aqueous solutions of the selected additives are employed in the form of the commercial product (cf. manufacturer specifications in Table 1.2).

The compositions according to the invention can be applied preferably by spraying via the leaves. Owing to the good plant compatibility, the application rate can be varied widely.

By comparative experiments, it was shown that, if additives are used which are not alkylglucosides or compounds of the formula II or III, it is not possible to achieve good or sufficiently satisfactory mixing compatibilities with the active compounds of the formula I.

By way of example, the following experiments illustrate the present invention and describe the corresponding formulations:

EXAMPLE 1

General Preparation Procedure

1–4 parts of the additive (see Tables 1.1 and 1.2) in aqueous solution are added to 8 parts of an aqueous active compound concentrate, and the mixture is vigorously stirred for 15 minutes. The added additives are employed in the form of the commercial products, in accordance with the recommendations for use recommended by the manufacturer. The commercial products are in most cases aqueous concentrates which comprise the respective additives in certain fixed concentrations. The solution is allowed to stand at room temperature for 10 minutes. The homogeneity of the formulation is subsequently assessed.

TABLE 1.1

List of the additives examined (comparative examples)

| Additive | Tradename | Emulsifier type/chemical name |
|---|---|---|
| A 01 | Tween ® 20 | Sorbitol oleate × 20 EO |
| A 02 | Citowett ® | Alkylphenol ethoxylate |
| A 03 | Synperonic ® 10/7 | i-C$_{10}$ oxoalcohol × 10 EO |
| A 04 | Silwett ® L-77 | Heptamethyltrisiloxane polyether |
| A 05 | Agral ® 90 | Nonylphenol ethoxylate |
| A 06 | Montane 20 | Sorbitan monolaureate |
| A 07 | HOE S 3474 | Tristyrenephenol × 20 EO |
| A 08 | Pluronic ® PE 6400 | PO/EO block copolymer having 40% EO; |
| A 9 | Emulan ® EL | Castor oil ethoxylate |
| A 10 | Emulan ® TO 2080 | Fatty alcohol ethoxylate |
| A 11 | Lutensit ® AE-P | Acidic phosphoric ester |
| A 12 | Lutensol ® A 3 N | C$_{12-14}$-fatty alcohol × 3 EO |
| A 13 | Lutensol ® AO 5 | C$_{13-15}$-oxoalcohol × 5 EO |
| A 14 | Lutensol ® AT 11 | C$_{16-18}$-fatty alcohol × 11 EO |
| A 15 | Lutensol ® ON 30 | C$_{10}$-oxoalcohol × 3 EO |
| A 16 | Lutensol ® TO 3 | C$_{13}$-oxoalcohol × 3 EO |
| A 17 | Lutensol ® FSA 10 | Fatty acid amide × 10 EO |
| A 18 | Lutensol ® FA 12 | Fatty amine × 12 EO |

TABLE 1.1-continued

List of the additives examined (comparative examples)

| Additive | Tradename | Emulsifier type/chemical name |
|---|---|---|
| A 19 | Plurafac ® LF 131 | PO/EO block copolymer; end group-capped |
| A 20 | 91 995-81-2 Rewoquat ® WE 18 | Di-(tallowcarboxyethyl)-hydroxy-ethyl-methylammonium methosulfate |
| A 21 | 86 088-85-9 Rewoquat ® W 90 | 1-Methyl-2-nortallowalkyl-3-tallow fatty acid amidoethylimidazolinium methosulfate |
| A 22 | 92 201-88-2 Rewoquat ® W 575 PG | 1-Methyl-2-norpalmalkyl-3-palmitic fatty acid amidoethylimidazolinium methosulfate |
| A 23 | 94 944-77-1 Rewoquat ® W 3690 PG | 1-Methyl-2-noroleyl-3-oleylamido-ethyl-imidazolinium methosulfate |
| A 24 | 91 995-81-2 Rewoquat ® WE 28 | Di(palmcarboxyethyl)-hydroxyethyl-methylammonium methosulfate |
| A 25 | Pluronic ® RPE 2520 | EO/PO block copolymer with 20% EO |
| A 26 | Pluronic ® RPE 3110 | EO/PO block copolymer with 10% EO |

Notes on the additives A 01–A 21 used:
A 01 and A 03: products of ICI Surfactants and Uniquema respectively
A 06: product of Seppic (Paris)
A 07: product of Hoechst-Clariant
A 02, A 08–A 19, A 25, A 26: products of BASF AG
A 20–A 24: quaternary ammonium salts, products of Witco.
Tween ®: Trademark of ICI America, Inc. for polyoxyethylene derivatives of sorbitan esters having the same reference number; international nonproprietary name: polysorbate (before: sorbimacrogol). Individual Tween11 ® brands are: polyethoxysorbitan laurate (Tween ® 20, Tween ® 21), palmitate (Tween ® 40), stearate (Tween ® 60, Tween ® 61), etc. Most Tween ® types are oily liquids (exception Tween ® 60, 61, 65) having excellent physiological and toxicological properties which, owing to their high hydrophilicity (HLB 10-16, 7), are soluble or dispersible in water. Moreover, they are soluble in many org. solvents. They are preferably employed for preparing O/W emulsions, and to a large extent in cosmetics, pharmacy and many other branches of industry as nonionic hydrophilic emulsifiers, solubilizers or wetting agents. Sources: Aldrich; Merck; Riedel.
Citowett ®: Wetting agent and tackifier based on alkylaryl polyglycol ethers. Source: BASF Aktiengesellschaft.
Pluronic ®: Trademark of BASF for liquid or solid nonionic polyalkylene glycols based on block polymers of ethylene oxide and propylene oxide. Lit.: Janistyn 1, 725–729.
Emulan ®: Selection of nonionic emulsifiers for the chemical industry based on fatty alcohols, alkyl phenol or fatty acids and their derivatives, for emulsifying solvents, waxes, fats and fatty oils, paraffin and mineral oils, for stabilizing emulsions and dispersions and as protection against rust. Source: BASF.
Lutensit ®: Selection of anionic surfactants or of mixtures of anionic with nonionic surfactants for the detergent industry and chemical industry. The anionic surfactants are alkylbenzenesulfonates, alkylphenol ethyl sulfates, fatty alcohol ether phosphates, alkylsulfonates or sulfated fatty acid condensation products. Source: BASF.
Lutensol ®: Nonionic surfactants for the detergent industry and chemical industry based on ethoxylated fatty alcohols, alkyl phenols or fatty amines and also alkylglucosides (see also individual references). Source: BASF.
Plurafac ® LF: Trademark of BASF. Fatty alcohol alkoxides; nonionic, low-foam and antifoam surfactants for detergents. Source: BASF.

TABLE 1.2

List of the additives which are added according to the invention

| Additive | Tradename | Emulsifier type/chemical name |
|---|---|---|
| B 01 | AG 6202 | 2-Ethylhexylglucoside |
| B 02 | Lutensol ® GD 70 Simusol ® SL 8 | Fatty alcohol glucoside Alkylglucoside CAS No. 68515-73-1 |
| | Simusol ® SL 62 | Alkylglucoside |
| B 05 | Rewoquat ® CPEM | Coconut pentaethoxymethylammonium methosulfate |

TABLE 1.2-continued

List of the additives which are added according to the invention

| Additive | Tradename | Emulsifier type/chemical name |
|---|---|---|
| B 06 | Rewoquat ® RTM 50 | Ricinoleic acid propylamidotrimethyl-ammonium methosulfate |
| B 07 | Protecol ® KLC 50 | Dimethyl-n-alkylbenzylammonium chloride |
| B 08 | Wettol ® EM 1 | Dodecylbenzenesulfonic acid, Ca salt |
| B 09 | Wettol ® EM 11 | Ca alkylarylsulfonate |
| B 10 | Emulphor ® OPS 25 | Octylphenol-(EO)$_{25}$ sulfate, Na salt |
| B 11 | Lutensit ® A-E S | Isononylphenol tetraethoxysulfate, Na salt |
| B 12 | Lutensit ® A-P S | Alkylsulfonate, Na salt |
| B 13 | ALBN 50 | Dodecylbenzenesulfonate, Na salt |

Notes on the additives used:

a) B 01–B 04: Additives from the group of the alkylglucosides B 01: Product of Akzo. The commercial product contains the additive 2-ethylhexylglucoside in a concentration of about 65% in water.
B 02, B 07, B 08: Product of BASF AG.
B 02: The commercial product contains the additive in a concentration of about 65% in water.
B 03 und B 04: Products of Seppic (Paris)

b) B 05–B 07: Additives from the group of the quaternary ammonium compounds
B 05: CAS No. 68 989-03-7
B 06: CAS No. 85 508-38-9 c) B 08–B 13: Additives from the group of the sulfates and sulfonates

Simulsol®: Alkyl polyglycol ether, alkyl polyglycol ester and alkanolamide/ethylene oxide adducts of partially unsaturated fatty alcohols, oleic and fatty acids based on sustainable natural fat raw materials. Use: surfactants for preparing detergents or as basic materials for formulating emulsifier systems. Source: Henkel, Germany.

Wettol®: Emulsifiers, wetting agents and dispersions for formulating emulsifiable concentrates or wettable powders as crop protection agents. Source: BASF.

Emulphor®: Selection of anionic emulsifiers for the chemical industry based on alkylbenzenesulfonates or ether sulfates. Source: BASF.

EXAMPLE 2

Comparative Examples

According to the general preparation process described in Example 1, the parts of the additives given in the table are in each case added to 8 parts of a highly concentrated solution of the active compound CCC of a concentration of 750 g/l. The results are shown in Table 2.1.

TABLE 2.1

Homogeneity of the aqueous mixtures

| Experiment No. | Additive | Parts | Homogeneity |
|---|---|---|---|
| 2.1 | A 01 | 2 | two phases |
| 2.2 | A 02 | 1 | two phases |
| 2.3 | A 03 | 2 | two phases |
| 2.4 | A 04 | 1 | two phases |
| 2.5 | A 05 | 1 | two phases |
| 2.6 | A 06 | 2 | two phases |

TABLE 2.1-continued

Homogeneity of the aqueous mixtures

| Experiment No. | Additive | Parts | Homogeneity |
|---|---|---|---|
| 2.7 | A 07 | 2 | two phases |
| 2.8 | A 08 | 1 | two phases |
| 2.9 | A 09 | 1 | two phases |
| 2.10 | A 10 | 2 | two phases |
| 2.11 | A 11 | 2 | two phases |
| 2.12 | A 12 | 2 | two phases |
| 2.13 | A 13 | 2 | two phases |
| 2.14 | A 14 | 2 | two phases |
| 2.15 | A 15 | 2 | two phases |
| 2.16 | A 16 | 2 | two phases |
| 2.17 | A 17 | 2 | two phases |
| 2.18 | A 18 | 2 | two phases |
| 2.19 | A 19 | 2 | two phases |
| 2.20 | A 20 | 2 | highly viscous inhomogeneous material |
| 2.21 | A 21 | 2 | highly viscous inhomogeneous material |
| 2.22 | A 22 | 2 | highly viscous inhomogeneous material |
| 2.23 | A 23 | 2 | highly viscous inhomogeneous material |
| 2.24 | A 24 | 2 | highly viscous inhomogeneous material |
| 2.25 | A 25 | 2 | two phases |
| 2.26 | A 26 | 2 | two phases |

EXAMPLE 3

Additives: Alkylglycosides

According to the process in Example 2, the parts given in the table of the alkylglucosides according to the invention and/or other auxiliaries are added in each case to 8 parts of a highly concentrated solution of the active compound CCC of a concentration of 750 g/l. The results are shown in Table 3.1. The concentration of the active compound CCC in the solution admixed with additives is, in the case of the mixture of 8 parts of active compound concentrate with 2 parts of the additives (mixing ratio 8:2) 600 g/l.

TABLE 3.1

Homogeneity of the aqueous mixtures

| Experiment No. | Additive (cf. Tab. 1.2) Type | Parts | Further additives (cf. Tab. 1.1 and 1.2) Type | Parts | Homogeneity |
|---|---|---|---|---|---|
| 3.1 | B 01 | 2 | — | — | clear homogeneous solution |
| 3.2 | B 01 | 1 | B 03 | 1 | clear homogeneous solution |
| 3.3 | B 01 | 1 | B 09 | 1 | clear homogeneous solution |
| 3.4 | B 01 | 1.2 | A 08 | 0.8 | clear homogeneous solution |
| 3.5 | B 02 | 2 | — | — | clear homogeneous solution |
| 3.6 | B 04 | 2 | — | — | clear homogeneous solution |
| 3.7 | B 01 | 1 | A 06 | 1 | clear homogeneous solution |
| 3.8 | B 01 | 0.8 | A 20 | 1.2 | clear homogeneous solution |

EXAMPLE 4

According to the process in Example 2, the parts given in the table of the quaternary ammonium compounds of the formula II according to the invention and/or other auxiliaries are added in each case to 8 parts of a highly concentrated solution of the active compound CCC of a concentration of 750 g/l. The results are shown in Table 4.1.

TABLE 4.1

Additives: quaternary ammonium compounds
Homogeneity of the aqueous mixtures

| Experiment No. | Additive (cf. Tab 1.2) Type | Parts | Further additives (cf. Tab. 1.1 and 1.2) Type | Parts | Homogeneity |
|---|---|---|---|---|---|
| 4.1 | B 05 | 2 | — | — | clear homogeneous solution |
| 4.2 | B 06 | 2 | — | | clear homogeneous solution |
| 4.3 | B 06 | 1.8 | A 03 | 0.8 | clear homogeneous solution |
| 4.4 | B 06 | 0.6 | A 19 | 0.8 | weakly turbid, homogeneous after filtration: clear |
| 4.5 | B 06 | 1.8 | A 02 | 0.8 | weakly turbid, homogeneous after filtration: clear |
| 4.6 | B 06 | 1.8 | Wettol ® EM 31* | 0.8 | slightly turbid, homogeneous after filtration: clear |
| 4.7 | B 07 | 1 | A 20 | 1 | clear homogeneous solution |
| 4.8 | B 07 | 2 | — | | clear homogeneous solution |

*W. EM 31 is a castor oil × EO and is a product of BASF AG;

In experiments 4.4–4.6, clear, stable solutions were obtained after filtration of impurities which were present owing to the production.

EXAMPLE 5

According to the process in Example 2, the parts given in the table of the sulfonates of the formula II according to the invention and/or other auxiliaries are added in each case to 8 parts of a highly concentrated solution of the active compound CCC of a concentration of 750 g/l. The results are shown in Table 5.1.

TABLE 5.1

Additives: sulfonates
Homogeneity of the aqueous mixtures

| Experiment No. | Additive Type | Parts | Further additives Type | Parts | Homogeneity |
|---|---|---|---|---|---|
| 5.1 | B 09 | 2 | — | — | clear homogeneous solution |
| 5.2 | B 09 | 1.2 | | | slightly turbid, homogeneous; after filtration: clear |
| 5.3 | B 09 | 1.2 | | | turbid homogeneous solution; after filtration: clear |
| 5.4 | B 10 | 1 | B 01 | 1 | clear solution |
| 5.5 | B 11 | 1 | B 01 | 1 | clear solution |
| 5.6 | B 13 | 1 | B 01 | 1 | clear solution |
| 5.7 | B 10 | 2 | | | clear solution |
| 5.8 | B 11 | 2 | | | clear solution |
| 5.9 | B 08 | 2 | 2-ethyl-cyclo-hexanol* | 30% | clear solution |
| 5.10 | B 12 | 2 | | | clear solution |

*The B 08 additive comprises, as solvent, 30% 2-ethylcyclohexanol

In experiments 5.2 and 5.3, clear, stable solutions were obtained after filtration of impurities which were present owing to the production. In the case of the additive B12 (experiment No. 5.10), a clear solution is advantageously obtained at elevated temperatures (in the range from 29–33° C.).

EXAMPLE 6

To investigate and determine the growth-regulating property of the test substances, test plants were grown in plastic containers (diameter about 12.5 cm; volume about 500 ml) on culture substrate which was supplied with sufficient nutrients. By the post-emergence method, the substances to be tested were sprayed, as an aqueous formulation, onto the plants. The growth-regulating effect which was observed was recorded at the end of the experiment by measuring the longitudinal growth. The data obtained in this manner were related to the longitudinal growth of the untreated plants.

Simultaneously with the reduction of the longitudinal growth, the color intensity of the leaves increased. Because of the increased chlorophyll content, it is anticipated that the rate of photosynthesis is likewise increased, and that the yield will consequently be higher.

EXAMPLE 7

As described in Example 6, biological experiments were carried out to investigate the growth-regulating properties of the compositions according to the invention, using alkylglucoside-containing additives (formulations from Examples 3.1 and 3.4). The individual data are shown in the tables below, the concentration being given in mg of active compound per container (AC/cont.).

TABLE 7.1

Reduction in longitudinal growth in summer wheat and summer barley

| | Reduction in longitudinal growth rel. (%) to the untreated control at the following application rates (AC/cont.) of the active compound CCC for summer wheat (SW) | | | |
|---|---|---|---|---|
| Formulation | 2.0 SW | 1.5 SW | 1.0 SW | 0.5 SW |
| Cycocel 720 (comparative product) | 74.0 | 76.5 | 78.0 | 83.5 |
| 3.1 | 67.0 | 69.5 | 71.0 | 77.0 |
| 3.4 | 68.0 | 71.0 | 71.0 | 74.0 |

Cycocel ® 720, commercial product of BASF AG, comprising 720 g/l CCC.
(Abbreviations:
AC = active compound;
SW = summer wheat).

Cycocel® 720, commercial product of BASF AG, comprising 720 g/l CCC. (Abbreviations: AC=active compound; SW=summer wheat).

As can be seen from Table 7.1, the formulations 3.1 and 3.4 according to the invention effect, at the same application rate, a more pronounced reduction of longitudinal growth of summer wheat, compared to the commercial product Cycocel 720.

EXAMPLE 8

Similarly to Example 7, biological experiments were carried out using formulations according to the invention in accordance with Examples 4:

TABLE 8.1

Reduction of longitudinal growth in summer wheat (SW) and summer barley (SB)

| | Reduction in longitudinal growth rel. (%) to the untreated control at the following application rates (AC/cont.) of the active compound CCC for summer wheat (SW) and summer barley (SB) | | | | | | | |
|---|---|---|---|---|---|---|---|---|
| Formulation | 2.0 SB | 1.5 SB | 1.0 SB | 0.5 SB | 2.0 SW | 1.5 SW | 1.0 SW | 0.5 SW |
| Cycocel 720 (comparative product) | 92.0 | 93.0 | 95.0 | 98.0 | 76.0 | 82.0 | 88.0 | 82.0 |
| 4.1 | 92.0 | 93.0 | 91.0 | 93.0 | 71.0 | 72.0 | 69.0 | 74.0 |
| 4.2 | 89.0 | 90.0 | 89.0 | 91.0 | 68.0 | 71.0 | 78.0 | 76.0 |

TABLE 8.2

Reduction of longitudinal growth in summer wheat (SW)

| | Reduction in longitudinal growth rel. (%) to the untreated control at the following application rates in kg/ha of the active compound CCC for summer wheat (SW) | |
|---|---|---|
| Formulation | 1.0 SW | 0.5 SW |
| Cycocel 720 (comparative product) | 84.0 | 91.0 |
| 4.3 | 78.0 | 81.0 |
| 4.6 | 78.0 | 78.0 |

EXAMPLE 9

Similarly to Example 7, biological experiments were carried out using formulations according to the invention in accordance with Example 5.

TABLE 9.1

Reduction of longitudinal growth of summer wheat

| | Reduction in longitudinal growth rel. (%) to the untreated control at the following application rates in kg/ha of the active compound CCC for summer wheat (SW) | |
|---|---|---|
| Formulation | 1.0 SW | 0.5 SW |
| Cycocel ® 720 (comparative product) | 84.0 | 91.0 |
| 5.1 | 78.0 | 81.0 |
| 5.2 | 81.0 | 82.5 |
| 5.3 | 79.5 | 82.5 |
| 5.4 | 81.0 | 82.5 |
| 5.5 | 82.5 | 82.5 |

EXAMPLE 10

Storage stability of additive-containing solutions of active compound at elevated temperatures An aqueous active compound-containing solution of the two active compounds CCC (content: 265 g/kg) and ethephon (content: 132 g/kg) was prepared with the various additives according to Table 1.2. The storage stability was determined at 54° C. after 14 days.

TABLE 10.1

Storage stability at 54° C. after 14 days
Active compound A: CCC; active compound B: ethephon

| Experiment No. | Additive (cf. Tab. 1.2) [g/kg] | | Other additives (cf. Tab. 1.2) [g/kg] | | Stability of active compound A [%] | Stability of active compound B [%] |
|---|---|---|---|---|---|---|
| 1 | B 01 | 250 | — | — | 100 | 97.3 |
| 2 | B 01 | 150 | PE 6400 | 100 | 98.4 | 99.4 |
| 3 | B 09 | 250 | — | — | 99.2 | 97.2 |
| 4 | B 10 | 250 | — | — | 100 | 98 |
| 5 | B 11 | 250 | — | — | 100 | 100 |
| 6 | B 12 | 250 | — | — | 100 | 97 |

The results show that the active compounds A and B are stable with addition of the additives according to the invention even at elevated temperatures and at storage over a period of 14 days.

We claim:

1. An aqueous homogeneous composition of an active compound concentration for regulating plant growth having an active compound concentration of at least 20%, which comprises
   a) at least one active compound of the formula I

(I)

$R^1$ is $C_1$–$C_4$-alkyl;
   $R^2$ is $C_1$–$C_4$-alkyl, cyclopentenyl, halo-$C_1$–$C_6$-alkyl; or $R^1$ and $R^2$ together are radical —$(CH_2)_5$—, —$(CH_2)_2$—O—$(CH_2)_2$— or —$(CH_2)$—CH=CH—$(CH_2)$—NH—;
   X is an anionic group; and
   b) at least one auxiliary selected from the group consisting of
      b1) alkylglucosides,
      b2) alkylsulfonates or alkylarylsulfonates of the formula II

(II), where $R^3$ is an aliphatic group having 6–24 carbon atoms, $C_6$–$C_{16}$-alkylphenoxypolyethoxy, $C_1$–$C_{16}$-alkylphenyl, $C_1$–$C_{16}$-alkylnaphthyl and M is a mono- or divalent cationic group.

2. A composition as claimed in claim 1, wherein the total concentration of active compounds is 30–70%.

3. A composition as claimed in claim 1, wherein the concentration of the active compound of the formula I is 5–60%.

4. A composition as claimed in claim 1 which comprises, as auxiliaries, an alkylglucoside selected from the group consisting of $C_4$–$C_{24}$-alkylglucosides, fattyalkylglucosides and polyglucosides.

5. A composition as claimed in claim 4 which comprises $C_8$–$C_{12}$-alkylglucosides, in particular ethylhexylglucoside.

6. A composition as claimed in claim 1, which comprises, as auxiliary, an alkylsulfonate or alkyarylsulfonate of the formula II.

7. A composition as claimed in claim 6 which comprises, as auxiliary, Octylphenyl-$(EO)_{25}$ sulfate Na salt, Isononylphenyl tetraethoxysulfate Na salt, Alkylsulfonate Na salt, Dodecylbenzenesulfonate Na salt, Dodecylbenzenesulfonic acid Ca salt, or Ca alkylarylsulfonate.

8. A composition as claimed in claim 1, which additionally comprises up to 30% of anionic, cationic or nonionic surfactants.

9. A composition as claimed in claim 1, which additionally comprises up to 35% of other agriculturally useful and/or activity-enhancing fertilizer salts.

10. A composition as claimed in claim 1, which additionally comprises up to 30% of alkylcarboxylic acids.

11. A composition as claimed in claim 1, which comprises N,N,N-trimethyl-N-β-chloroethylammonium chloride (CCC) as active compound of the formula I.

12. A composition as claimed in claim 1, which comprises N,N-dimethylpiperidium chloride as active compound of the formula I.

13. A composition as claimed in claim 1, which comprises ethephon as further active compound for treating plants.

14. A process for regulating plant growth, which comprises treating the plants with a composition as claimed in claim 1.

15. A process as claimed in claim 14, wherein the plants are treated at an application rate of an active compound of less than 1.5 kg/ha per application.

16. A process as claimed in claim 15, wherein the application rate is 0.1–1 kg/ha.

17. A method for reducing the application rate in the agricultural utilization of an active compound of the formula I, as specified in claim 1, by using at least one compound selected from the group consisting of a) alkylglucosides, b) alkylsulfonates or alkylarylsulfonates of the formula II $$R^3-SO_3^-M^{(+,++)} \tag{II},$$

where $R^3$ is an aliphatic group having 6–24 carbon atoms, $C_6$–$C_{16}$-alkyl-phenoxypolyethoxy, $C_1$–$C_{16}$-alkyl-phenyl, $C_1$–$C_{16}$-alkyl-naphtyl and M is a mono- or divalent cationic group; as an auxiliary in an aqueous composition for regulating plant growth, wherein said aqueous composition comprises an active compound concentrate of at least one compound of formula I as defined in claim 1.

18. A method for preparing stable monophasic aqueous active compound concentrates which comprise an active compound of the formula I, as specified in claim 1, comprising the step of combining said active compound with at least one auxiliary selected from the group consisting of a) alkylglucosides, and b) alkylsulfonates or alkylarylsulfonates of the formula II, as specified in claim 1.

* * * * *